(12) United States Patent  
Gochar, Jr.

(10) Patent No.: US 7,800,009 B2  
(45) Date of Patent: Sep. 21, 2010

(54) AIR SEPARATOR CONVEYOR AND VISION SYSTEM

(75) Inventor: Joseph P. Gochar, Jr., Baltimore, MD (US)

(73) Assignee: Logical Systems Incorporated, Baltimore, MD (US)

( * ) Notice: Subject to any disclaimer, the term of this patent is extended or adjusted under 35 U.S.C. 154(b) by 162 days.

(21) Appl. No.: 11/927,795

(22) Filed: Oct. 30, 2007

(65) Prior Publication Data

US 2009/0107896 A1    Apr. 30, 2009

(51) Int. Cl.  
*B07C 5/00* (2006.01)

(52) U.S. Cl. .................. 209/576; 209/577; 209/580

(58) Field of Classification Search ......... 209/928, 209/906, 925, 934, 929, 576, 577, 580; 198/395, 198/380, 341.01; 414/676, 86  
See application file for complete search history.

(56) References Cited

U.S. PATENT DOCUMENTS

| | | | |
|---|---|---|---|
| 3,812,947 A * | 5/1974 | Nygaard | 198/617 |
| 4,196,811 A | 4/1980 | Pilesi et al. | |
| 4,295,200 A * | 10/1981 | Johnson | 702/82 |
| 4,308,959 A | 1/1982 | Hoover et al. | |
| 4,394,683 A | 7/1983 | Liptay-Wagner et al. | |
| 4,709,800 A | 12/1987 | Olsen | |
| 4,882,498 A | 11/1989 | Cochran et al. | |
| 4,915,237 A | 4/1990 | Chang et al. | |
| 4,924,107 A | 5/1990 | Tucker | |
| 4,946,025 A | 8/1990 | Murphy | |
| 4,972,093 A | 11/1990 | Cochran et al. | |
| 5,051,825 A | 9/1991 | Cochran et al. | |

(Continued)

FOREIGN PATENT DOCUMENTS

EP    0572336 B1    1/1993

(Continued)

OTHER PUBLICATIONS

Inspector Product Literature, IC Vision, Feb. 22, 2001, 16 pages.

(Continued)

*Primary Examiner*—John Q. Nguyen  
*Assistant Examiner*—Michael E. Butler  
(74) *Attorney, Agent, or Firm*—Wood, Herron & Evans, LLP

(57) ABSTRACT

A system for accurately determining whether a work piece such as a plastic molded bottle cap is defective from quality norms and removing those defective pieces from a stream of work pieces includes a feed conveyor for serially delivering work pieces where adjacent work pieces are in contact with each other. The feed conveyor delivers these work pieces onto an inspection conveyor with a plurality of air holes. Air is forced through the air holes to impinge upon the work piece and thus rapidly accelerate them away from the adjacent work piece it was in contact with and move through an inspection station. An air blower provides pressurized air through the air holes to continue accelerating and separating the work pieces as they move. The inspection station includes a camera to image each work piece. The camera communicates these images to a processing unit such as a computer that can rapidly compare the image to a set of quality control standards each work piece should meet.

16 Claims, 8 Drawing Sheets

U.S. PATENT DOCUMENTS

| | | |
|---|---|---|
| 5,068,799 A | 11/1991 | Jarrett, Jr. |
| 5,072,127 A | 12/1991 | Cochran et al. |
| 5,095,204 A | 3/1992 | Novini |
| 5,172,005 A | 12/1992 | Cochran et al. |
| 5,297,667 A * | 3/1994 | Hoffman et al. .............. 198/493 |
| 5,303,811 A | 4/1994 | Haley |
| 5,331,151 A | 7/1994 | Cochran et al. |
| 5,365,084 A | 11/1994 | Cochran et al. |
| 5,440,385 A | 8/1995 | Fein et al. |
| 5,451,773 A | 9/1995 | Triner et al. |
| 5,524,746 A * | 6/1996 | Massen et al. .............. 198/443 |
| 5,581,074 A | 12/1996 | Yoshida |
| 5,591,462 A | 1/1997 | Darling et al. |
| 5,592,286 A | 1/1997 | Fedor |
| 5,695,302 A | 12/1997 | Hilbish |
| 5,699,152 A | 12/1997 | Fedor et al. |
| 5,745,593 A | 4/1998 | Wahawisan et al. |
| 5,805,279 A | 9/1998 | Palombo et al. |
| 5,911,003 A | 6/1999 | Sones |
| 5,936,353 A | 8/1999 | Triner et al. |
| 6,384,421 B1 | 5/2002 | Gochar, Jr. |

FOREIGN PATENT DOCUMENTS

| | | |
|---|---|---|
| GB | 2005826 A | 4/1979 |
| GB | 2066455 A | 7/1981 |
| GB | 2078948 A | 1/1982 |
| GB | 2136954 A | 9/1984 |
| JP | 11108853 | 4/1999 |

OTHER PUBLICATIONS

British Search Report, May 16, 2001, 1 page.

* cited by examiner

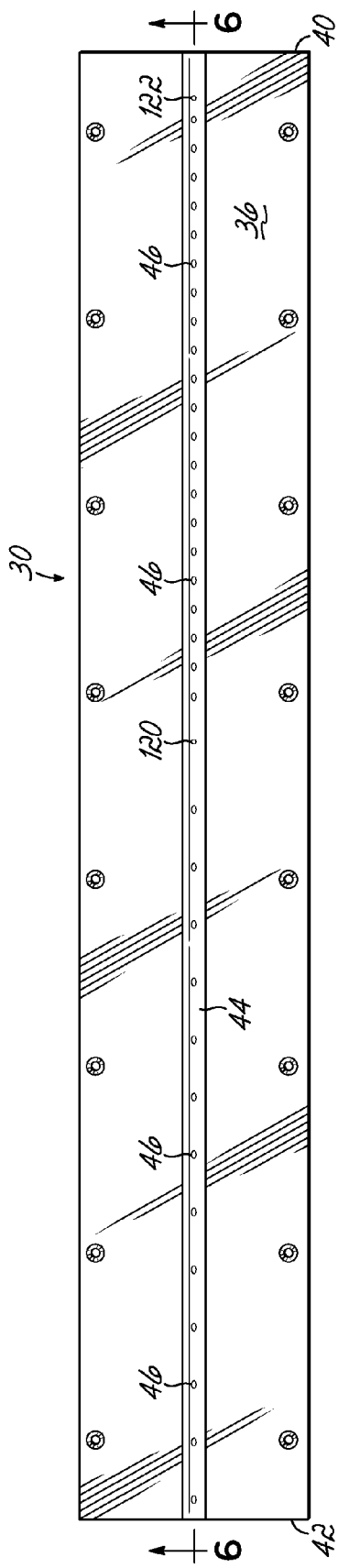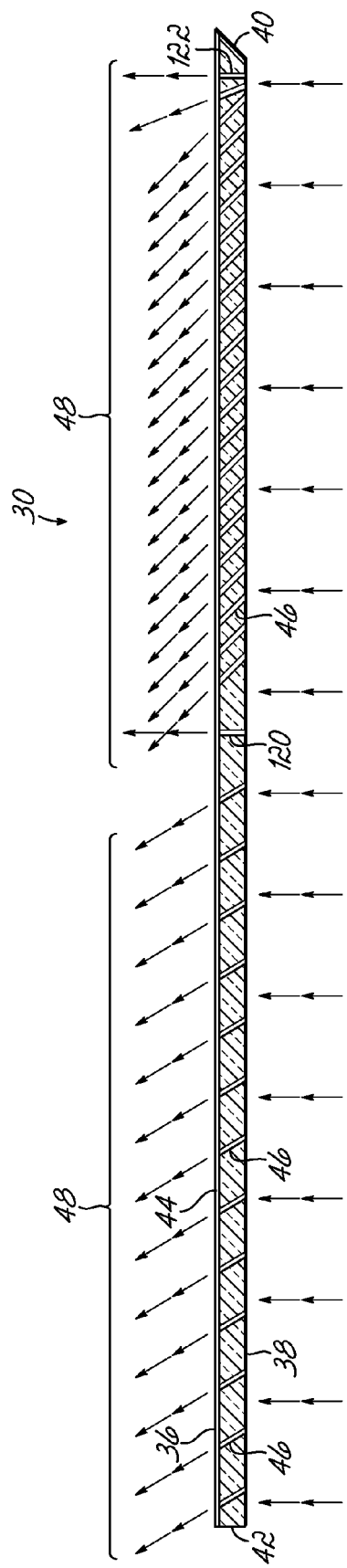
FIG. 5
FIG. 6

AIR SEPARATOR CONVEYOR AND VISION SYSTEM

FIELD OF THE INVENTION

This invention relates to article inspection systems and particularly to vision systems for inspecting work pieces such as plastic molded closure caps for containers and the like.

BACKGROUND

During the manufacture of many parts such as plastic molded closure caps, a number of defects in the closure cap may exist which should cause the cap to be rejected. Commonly, closure caps of this type have a liner inserted therein against the inner surface of an end wall of the cap. Typically, the cap has a skirt projecting annularly from the peripheral rim of the end wall and the skirt may include a closure or sealing mechanism such as threads for cooperation with mating threads around the neck of a bottle, container, or the like. Examples of defects in such closure caps include a liner which is positioned off-center within the closure, a missing liner, a malformed liner (commonly referred to as a "moon-cut liner"), a cap which is asymmetric or off-round, a cap having an edge broken or flashing on the edge from extraneous plastic material, a pull tab defect on the liner caps with excessively large "gates" resulting from the molding process, or other similar problems. Such flaws or defects are sometimes produced during the manufacturing process, or as a result of contamination or damages after manufacture but prior to the filling of the container.

Machine vision systems represent one technology for acquiring or sensing an image of at least a selected portion of a work piece, such as a cap as previously described, through an electronic sensor or camera. The image generated by the camera is then analyzed by a computer program for one or more of the above-described defects. Vision systems are commonly used to determine the existence of any marks or defects in the image of the cap and the acceptability of any such marks or defects by use of a vision computer as described.

While human vision may outperform its automatic equivalent in the ability to analyze very complex, everyday scenes, when it comes to repeated tasks, such as the inspection of plastic molded caps over and over again, a human observer understandably tires, loses concentration, and makes mistakes. Machine vision inspection of such articles is known to provide some important advantages, including sophisticated image processing/analysis, repeatable performance, image acquisition for diagnosis and set up, ability to inspect a variety of articles in large tolerance and required part placement. Moreover, at inspection rates of up to 1600 parts per minute or more, each part or cap spends on the order of 33 milliseconds at an inspection station. At such speeds, only a machine vision system is fast enough to reliably and repeatedly inspect such articles.

While known vision systems have the above described advantages for inspecting articles such as plastic molded caps and the like, they do have specific and significant limitations. Vision systems typically rely on video cameras to image the article to be inspected and detect any flaws. The resolution of the camera, or its ability to detect a flaw, is directly related to its ability to capture an accurate and reliable image of each individual cap, article, or similar item. Typically, plastic molded caps are manufactured by the hundreds of thousands and each individual cap must be inspected by the vision system for quality control purposes. The caps are typically gathered in an accumulated mass and are, at best, similarly oriented on a flat surface. For accurate vision inspection and detection of flaws, the vision system must be able to precisely and accurately produce an image of each individual cap without interference from the surrounding environment or other caps. Furthermore, inspection rates required of such systems mandate that the individual images be serially produced, analyzed, and acted upon accordingly for each individual cap, once again without interference, for accurate detection of relatively small flaws or problems.

One problem in efficiently creating photographic records of each plastic molded cap is providing enough separation between adjacent caps on a conveyor leading to the vision system. One solution is disclosed in U.S. Pat. No. 6,384,421, assigned to the assignee of this invention and hereby incorporated by reference entirely. Vision systems of this type separate caps by funneling a mass of caps into a single-file conveyor belt and then providing a vertical incline or ramp to accelerate and separate each cap from adjacent caps. This process is effective, but often requires a relatively large space and floor space in most industrial settings is limited. Therefore, an improved vision system that allows high-precision and high-speed inspection while occupying a small foot-print is needed.

SUMMARY OF THE INVENTION

This invention provides a machine and method for inspecting masses of industrial work pieces such as plastic molded bottle caps and other articles. This invention overcomes the limitations and problems associated with known inspection systems.

In a first embodiment, this invention is a system for accurately determining whether a work piece such as a plastic molded bottle cap is defective from quality norms and removing those defective pieces from a stream of work pieces. The system includes a feed conveyor for serially delivering work pieces where adjacent work pieces are in contact with each other. The feed conveyor delivers these work pieces onto an inspection conveyor that is generally horizontal. Adjustable guide rails and a guide rail cover create a closed passage just large enough for the work pieces to flow through without impediment. The inspection conveyor may also have one or more machined grooves to allow slightly defective work pieces to flow through the passage without dragging or getting stuck.

The inspection conveyor is provided with a number of angled air holes there through and the system also contains a separate air jet near the feed conveyor. The air jet receives a signal from a trigger such as a photoelectric switch that a work piece has entered the opening of the passage, and a control mechanism opens a high speed valve, allowing high pressure air to blow through the air jet and onto the rear surface of the work piece. The work piece is thus rapidly accelerated away from the adjacent work piece it was in contact with and moves through the passage. An air blower provides pressurized air through the air holes to continue accelerating and separating the work pieces as they move from the air jet through the passage. This air blower is controlled using a pressure sensor and a variable speed drive mechanism for the air blower's motor. This system is customizable for a variety of shapes and sizes of work pieces that need to be inspected for flaws as well as other operating parameters.

The inspection conveyor in one embodiment is generally made with a translucent plastic material that transmits some light. In the middle of the passage, the guide rails and the guide rail cover each have an opening where an inspection station is located. This inspection station includes at least one camera and one light source. The light source can be any kind of light that illuminates the work piece such as a bottle cap, and one embodiment uses an infrared light. The light source is located under the inspection conveyor and lights the underside of each work piece. The camera is located above the inspection conveyor and light source and is oriented perpendicular to the inspection conveyor so that a full image of each work piece can be recorded as the work piece moves through the inspection station. The camera is timely activated by a trigger such a photoelectric switch that determines exactly when a work piece is in position to be photographed.

The camera communicates these images to a processing unit such as a computer that can rapidly compare the image to a set of quality control standards each work piece should meet. The processing unit analyzes each image for defects and controls a rejection mechanism located just after the camera and light source in the inspection station. This rejection mechanism can be another air jet or mechanical arm that pushes work pieces determined to be defective out of the passage through the opening at the inspection station.

A second embodiment of the invention includes all the same elements as the first embodiment, but in this embodiment a portion of the inspection conveyor is replaced with a glass window at the inspection station. In this embodiment the light source and the camera can be switched so that the camera takes images from beneath the work pieces sitting on the inspection conveyor, and the light source illuminates the work pieces from above the inspection conveyor. Alternatively, this second embodiment could allow for two cameras positioned one above and one below the inspection conveyor instead of one camera and a light source. With two cameras, more work pieces that do not transmit light well can be analyzed and inspected. This second embodiment will allow for different kinds of work pieces to be inspected and sorted by this invention.

This invention overcomes the above-described disadvantages of known vision inspection systems by providing a precision-controlled separation distance and time between each of a series of work pieces such as plastic molded bottle caps. The level of air pressure delivered by the air jet and the air blower as well as the angle of the air holes disposed through the inspection conveyor can all be altered to fit the needs of a specific set of work pieces, thereby giving the current invention much more precision than known gravity-driven inspection systems in a smaller work space. The processing and analyzing rates are not affected by the changes from known systems, as the current invention can handle the inspection of up to 1600 work pieces per minute, depending on the work piece and the air pressure configuration.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

FIG. 5 is a top view of an inspection conveyor according to the first embodiment of this invention.

FIG. 6 is a cross-sectional side view of the center of the inspection conveyor taken along line 6-6 of FIG. 5 with arrows depicting how pressurized air flows on both sides of the inspection conveyor.

DETAILED DESCRIPTION

Figure 1:
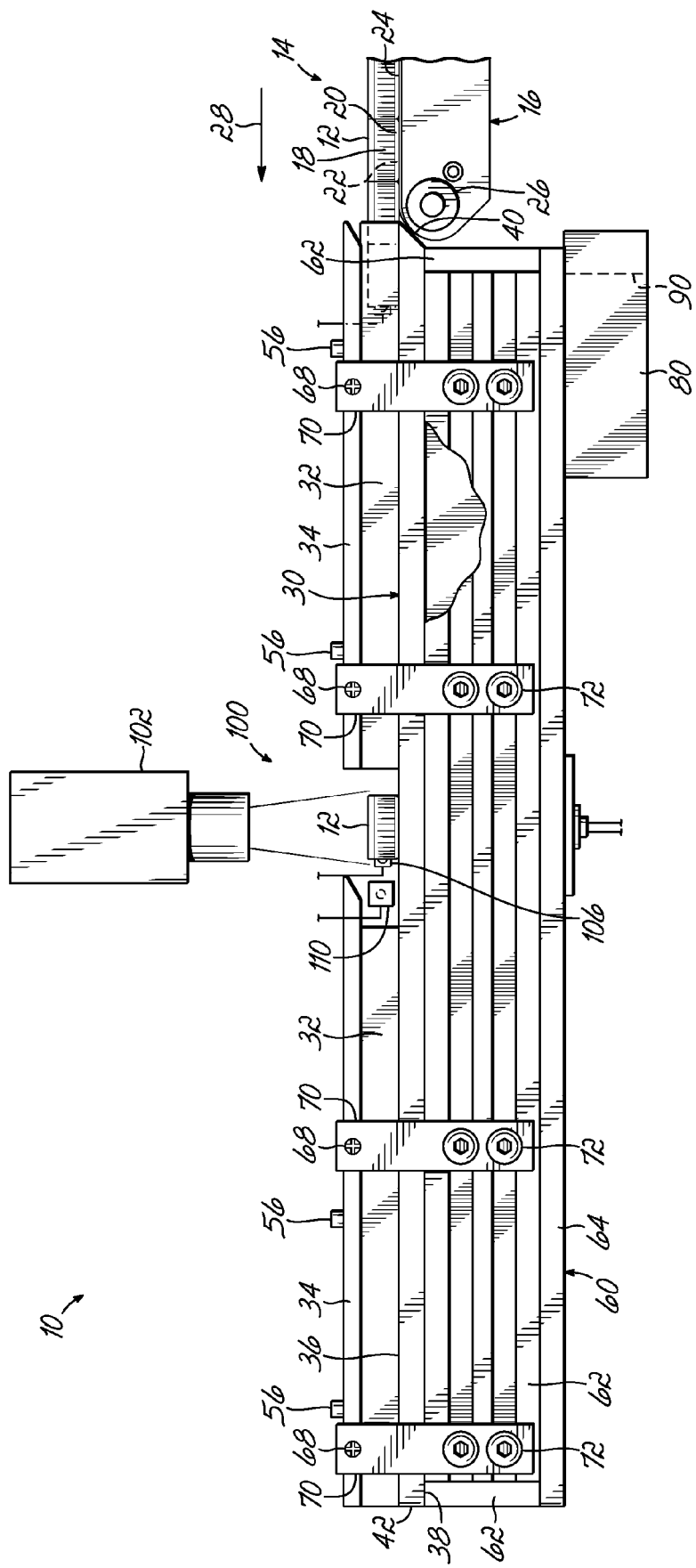
FIG. 1 is a front view of a first embodiment of the air separator conveyor and inspection system according to this invention.

Referring to FIGS. 1-9, a first embodiment of this invention of an air conveyor vision inspection system and associated method for industrial work pieces is shown. The inspection system 10 is used to individually inspect each of a number of work pieces 12 and determine if each work piece 12 meets quality control standards. These work pieces 12 can be any variety of industrially produced items, such as plastic molded bottle caps as shown in FIGS. 1-11. For bottle caps 12, a batch 14 of the caps 12 is created using an injection molding process and then delivered by a feed conveyor 16 or other means to the inspection system 10. Bottle caps 12 made in this manner typically include a peripheral skirt 18 projecting from a base or end wall 20 and a liner 22 may also be inserted into the cap 12.

As shown in FIG. 1, the inspection system 10 processes work pieces or caps 12 from a feed conveyor 16, which comprises a belt 24 trained to travel around at least two rotating rollers 26 (of which one is shown in FIG. 1), one of which drives the belt 24. The feed conveyor 16 delivers caps 12 serially in the direction of arrow 28 to the system 10.

Figure 2:
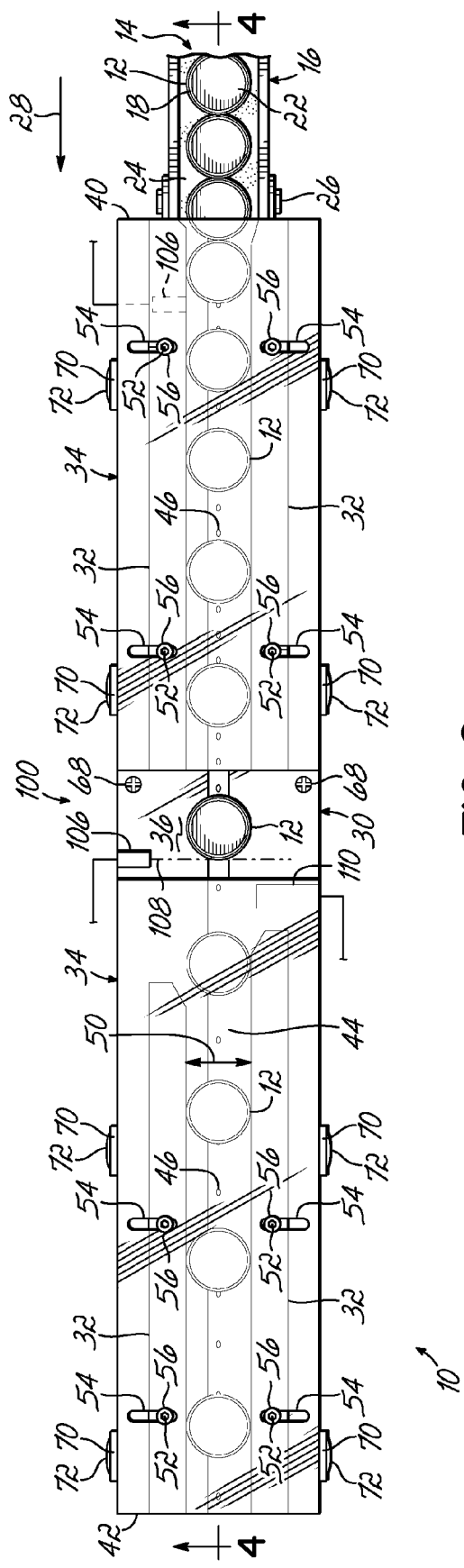
FIG. 2 is a top view of the first embodiment of this invention showing work pieces flowing through the system's passage and inspection station.

The structural features of this first embodiment of the invention are shown in detail in FIGS. 1-4. Referring to FIGS. 1-2, the system 10 includes an inspection conveyor 30, at least two guide rails 32, and a guide rail cover 34. The inspection conveyor 30 is generally horizontal, but may also be set at an incline in other embodiments. The inspection conveyor 30 receives work pieces 12 onto a top surface 36 at a first end 40 and the work pieces 12 continue moving toward a second end 42 of the inspection conveyor 30. The inspection conveyor 30 is generally planar on the top surface 36 as well as a bottom surface 38. As shown in more detail in FIGS. 5-6, the inspection conveyor 30 further includes a shallow groove 44 running lengthwise from the first end 40 to the second end 42. This shallow groove 44 is designed to allow work pieces or caps 12 with minor acceptable defects such as "high gate" to move down the inspection conveyor 30 without dragging or getting stuck. Air holes 46 extend through the inspection conveyor 30 from the bottom surface 38 to the top surface 36 and run lengthwise down the inspection conveyor 30. These air holes 46 may be vertical or angled and may have any appropriate inner diameter for delivering pressurized air as shown by arrows 48 in FIG. 6.

The guide rails 32 are coupled to the inspection conveyor 30 on the top surface 36 by placing the guide rails a certain distance 50 apart from each other, this distance 50 being at least the width of work pieces 12 being inspected plus an allowable tolerance for the passage of irregularly shaped work pieces 12. The guide rails 32 have projections 52 such as pegs extending away from the inspection conveyor 30. The guide rail cover 34 is shown in FIG. 2 as a generally flat and horizontal body with slots 54 designed to accept the projections 52. The guide rail cover 34 can then be coupled to the guide rails 32 by tightening a nut 56 on a projection 52 if the projection 52 is threaded, or by any alternative appropriate means depending on the projections 52. Thus connected, the inspection conveyor 30, guide rails 32, and guide rail cover 34 create an air tunnel or passage 58 adapted to accept work pieces 12 of a given shape and size (see FIG. 8 for detail).

Figure 3:
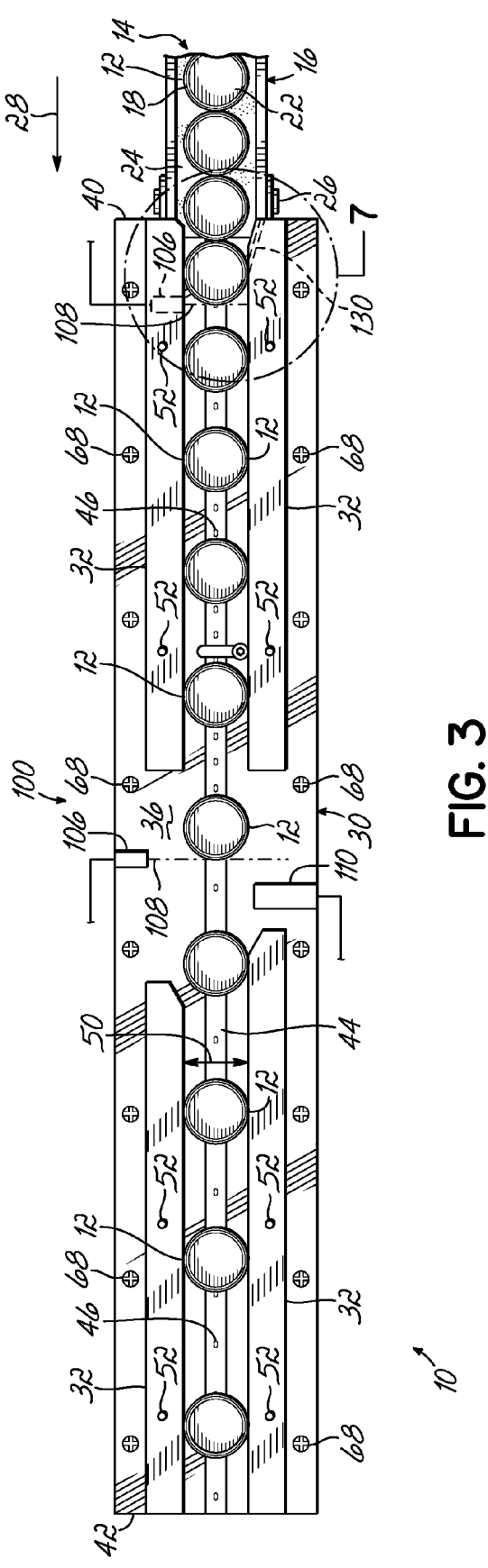
FIG. 3 is a top view of the first embodiment of this invention with the guide rail cover removed from the top of the device.
Figure 4:
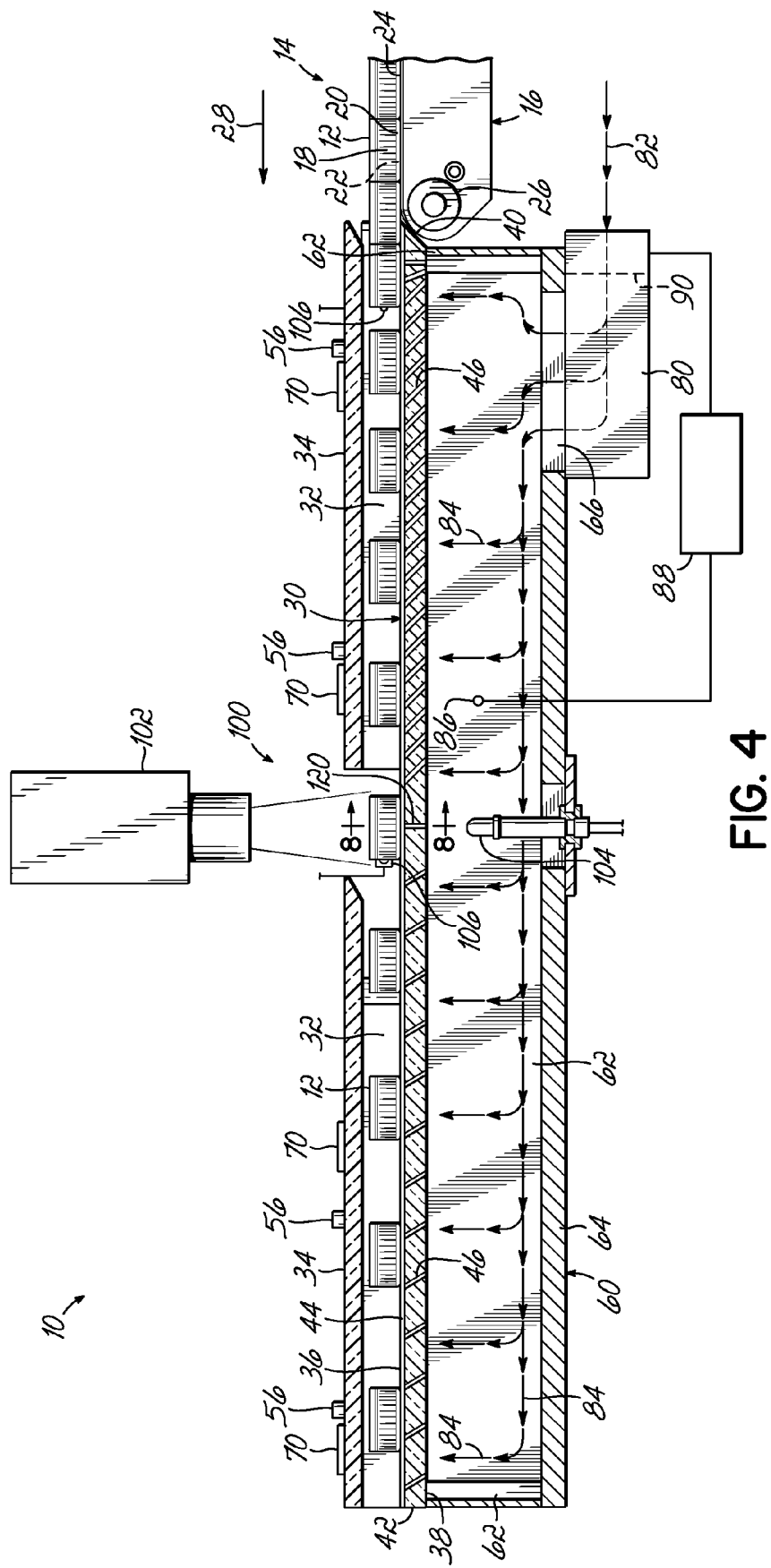
FIG. 4 is a cross-sectional side view of the first embodiment of this invention illustrating the flow of work pieces and pressurized air.
Figure 8:
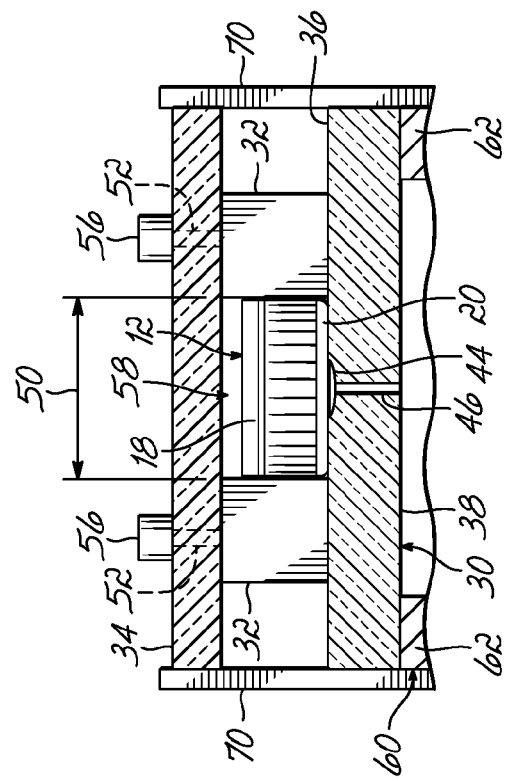
FIG. 8 is a cross-sectional view taken along line 8-8 of FIG. 4 looking toward the first end of the inspection conveyor from the inspection station.

In the first embodiment shown in FIGS. 1 and 4, the inspection conveyor 30 rests on top of and is coupled to the side walls 62 of an air delivery chamber 60. This chamber 60 may be any size or shape, but is shown in FIGS. 1-4 as a rectangular box with side walls 62, a bottom wall 64, and an inlet 66 connected an air blower 80. The inspection conveyor 30 can be coupled to the side walls 62 using a plurality of screws 68 or other connectors. The entire system 10 is further stabilized and coupled together with mounting brackets 70 that are attached to the guide rail cover 34 and the side walls 62 by screws 68 or by other acceptable means such as T-nuts 72.

The delivery rate or speed of the feed conveyor 16 depends upon the required inspection rate for the work pieces 12, the size of the work pieces 12, and other relevant factors. For example, if the work pieces 12 are plastic molded caps 12 with a diameter of 1.1 inches and an inspection rate of 1600 caps per minute is desired, the feed conveyor 16 will operate at about 147 feet per minute maximum speed for the delivery of the caps 12 to the first end 40 of the inspection conveyor 30. The corners of the guide rails 32 and guide rail cover 34 may be chamfered or beveled as shown in FIGS. 1-4 to facilitate work pieces 12 entering the passage 58. The inspection conveyor 30, guide rails 32, and guide rail cover 34 are all made of a smooth and translucent material such translucent UHMW plastic which is very wear resistant in one embodiment of this invention.

In FIG. 4 the cross-section of the system 10 is shown to emphasize the air flow driving the work pieces 12. The air blower 80 takes ambient air as shown by arrows 82 through a filter go (not shown in detail) to keep dust particles out of the inspection system 10. The air blower 80 then pumps pressurized air into the air delivery chamber 60 through an inlet 66 as depicted by arrows 84. A pressure sensor 86 inside the air delivery chamber 60 measures the air pressure being delivered by the air blower 80 and sends this information to a controller 88. This controller 88 maintains the desired air pressure by adjusting a variable-speed drive mechanism (not shown) of the air blower 80 to increase or decrease the pressure as necessary. The controller 88 can also monitor if the air blower filter go becomes dirty and ineffective and give users a signal to change that filter go. The controller 88 can be any appropriate computer or device for the tasks described, including a PLC to create the control algorithm. Also, the passage 58 created by the inspection conveyor 30, guide rails 32, and guide rail cover 34 creates a "wind tunnel effect," which amplifies the effect the pressurized air has on each work piece 12 and reduces the need for large volumes of pressurized air. The airflow produced by the air blower 80 and delivered to the inspection conveyor 30 can be adjusted depending upon the operating parameters of the system 10 and the work pieces 12. One adjustment may include the removal of portions of the guide rails 32 proximate a downstream portion of the passage 58 to alleviate congestion of the caps in the passage by allowing for induced airflow for more volume of air through the system.

Positioned intermediate the first end 40 and the second end 42 of the inspection conveyor 30 is an inspection station 100, which includes a camera 102 mounted generally perpendicular to and above the top surface 36 of the inspection conveyor 30. The inspection station 100 further includes a light source 104 mounted opposite the camera 102 and underneath the inspection conveyor 30, which is made of translucent material as described above. In the current embodiment, the light source 104 may be an infrared or other color LED strobe light which is preferably adjustable to provide a frequency that is appropriate for the inspection rate of the work pieces 12, typically as high as 1600-2000 work pieces per minute. Backlighting of the work pieces 12 by the light source 104 in many instances allows for better contrast and image quality by the camera 102. An infrared light source 104 provides increased imaging capabilities for particular colors of work pieces 12 such as white. However, other light sources and imaging arrangements are contemplated within this invention.

A trigger 106 such as a photoelectric switch shown in FIGS. 1-4 activates the camera 102 and light source 104. When the leading edge of a work piece 12 crosses the plane (depicted by line 108) of the trigger 106, the trigger 106 sends a signal to a processing unit such as a computer (not shown). The processing unit coordinates the operation of the camera 102 and the light source 104 and the camera 102 captures an image of the work piece 12 illuminated by the light source 104. The camera is operably coupled to the processing unit and sends the images immediately to the processing unit for analyzing. The processing unit then compares the image to certain quality control standards set by the user. In the case of bottle caps 12, defects such as off-center or missing liners, a moon-cut liner, or a cap that is not properly shaped can all be detected. If any undesirable defect is detected by the processing unit, the processing unit sends another signal to a rejection mechanism 110 that is operably coupled to the processing unit. The rejection mechanism 110 may be any one of a number of items designed to remove a work piece 12 from the passage 58 or stream of work pieces. For example, an air jet 110 as shown in FIGS. 1-4 and 9 may be positioned immediately following the camera 102 and light source 104 locations in order to blow a puff of pressurized air in the direction of arrow 112 (FIG. 9) to remove a defective work piece 114. The guide rails 32 and guide rail cover 34 may have an opening as shown in FIGS. 1-9 to allow the inspection station 100 to capture images and remove selected defective work pieces 114 from the passage 58. Again at the end of the inspection station 100, the corners of the guide rails 32 and guide rail cover 34 may be chamfered or beveled as shown in FIGS. 1-4 to facilitate work pieces 12 entering the passage 58.

The cross-section of the inspection conveyor 30 is shown in FIG. 6. The air holes 46 may be configured in any appropriate manner, but the first embodiment depicted in FIG. 6 provides a typical arrangement. Most of the air holes 46 are angled approximately 45 degrees from vertical, but this angle may be changed depending on the work pieces 12 being moved and other parameters. One vertical air hole 120 is located at the inspection station 100, and this vertical hole 120 keeps work pieces 12 moving at a steady rate. As shown in FIG. 6, the air holes 46 disposed between the first end 40 and the inspection station 100 can have a larger diameter and be spaced closer together than the air holes 46 disposed between the inspection station 100 and the second end 42. The air holes 46 disposed after the inspection station 100 may also have a shallower angle than the air holes 46 before the inspection station 100. This allows for work pieces 12 to be accelerated at a higher rate when the work pieces 12 need to be separated. Separation between the work pieces 12 is important to provide an accurate image and subsequent analysis of each work piece 12 without interference from adjacent work pieces 12. For example, the air holes 46 upstream from the inspection station 100 may be spaced 0.50 inches apart and have inner diameters of 0.078 inches while the air holes 46 downstream from the inspection station 100 may be spaced 1.00 inches apart and have inner diameters of 0.062 inches. One other feature of the air hole arrangement shown in FIG. 6 is the air holes 122 near the first end 40 may start vertical and progressively gain more angle for each adjacent hole 122 until the desired 45 degree or similar angle is achieved, but this arrangement is optional.

Figure 7:
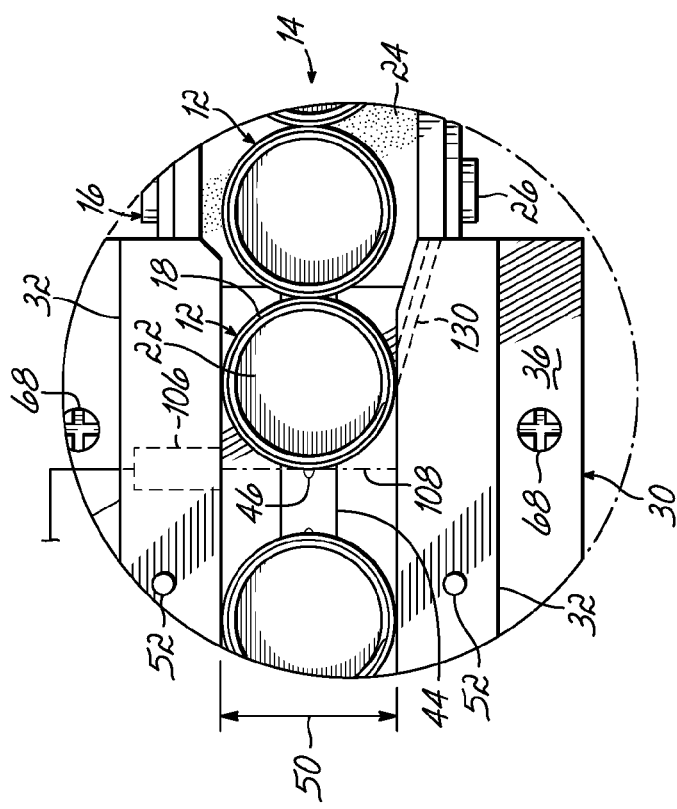
FIG. 7 is an enlarged detailed top view of a the first end of the inspection system where a feed conveyor delivers work pieces to the passage and an air jet separates these work pieces.
Figure 9:
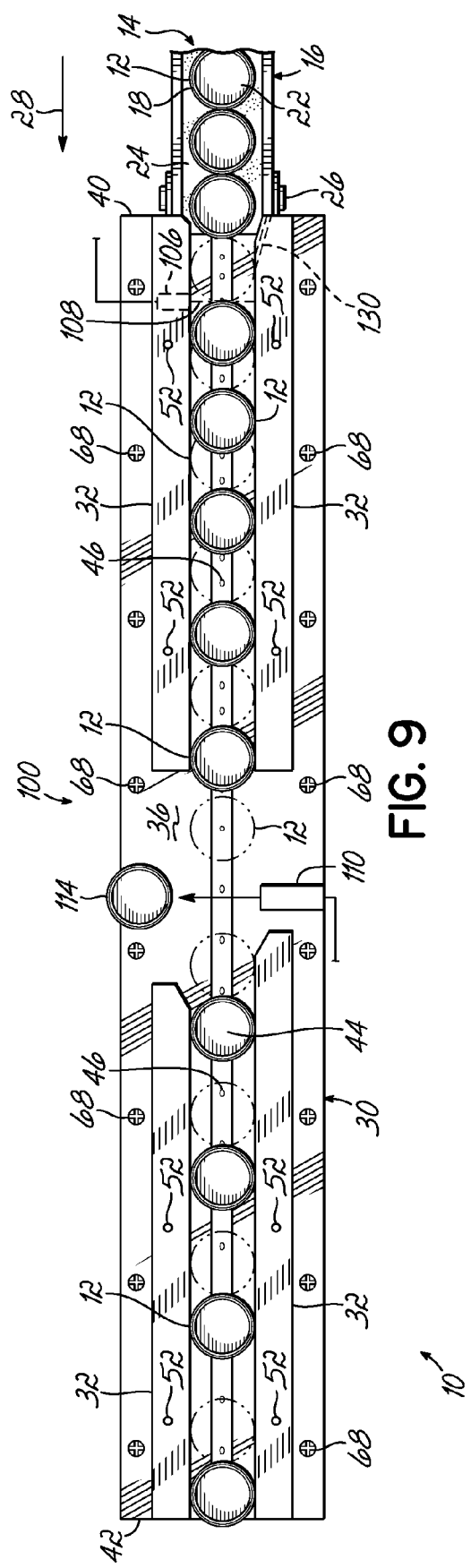
FIG. 9 is a schematic representation of the first embodiment where a defective work piece is being removed from the passage.

As depicted by FIGS. 3 and 7, the front end of the system 10 has additional elements. An air jet 130 is located through at least one of the guide rails 32 to initially accelerate and separate entering work pieces 12 from adjacent work pieces 12. The air jet 130 includes a trigger 106 such as a photoelectric switch, an air valve (not shown), and a control mechanism (not shown) such as the PLC controller 88 for the air blower 80. In fact, the PLC controller 88 can be configured with a high speed module that can control and provide pulses of pressurized air in one millisecond increments. Once an entering work piece 12 crosses the plane (line 108) of trigger 106, the trigger 106 sends a signal to the control mechanism, which in turn opens the air valve and sends a blast of pressurized air into the rear side of the work piece 12. The air valve must be able to cycle at very high rates of speed for this application, and a MAC air valve that can open and close in less than five milliseconds is an appropriate example. Just like the other air holes 46, the pressure to the air jet 130 can be controlled and modified for various sizes and weights of work pieces 12. The position of the trigger 106 may be modified in a similar fashion. Additional air jets 130 can be included one on or both of the guide rails 32 at downstream locations proximate the inspection station 100 as needed.

Figure 10:
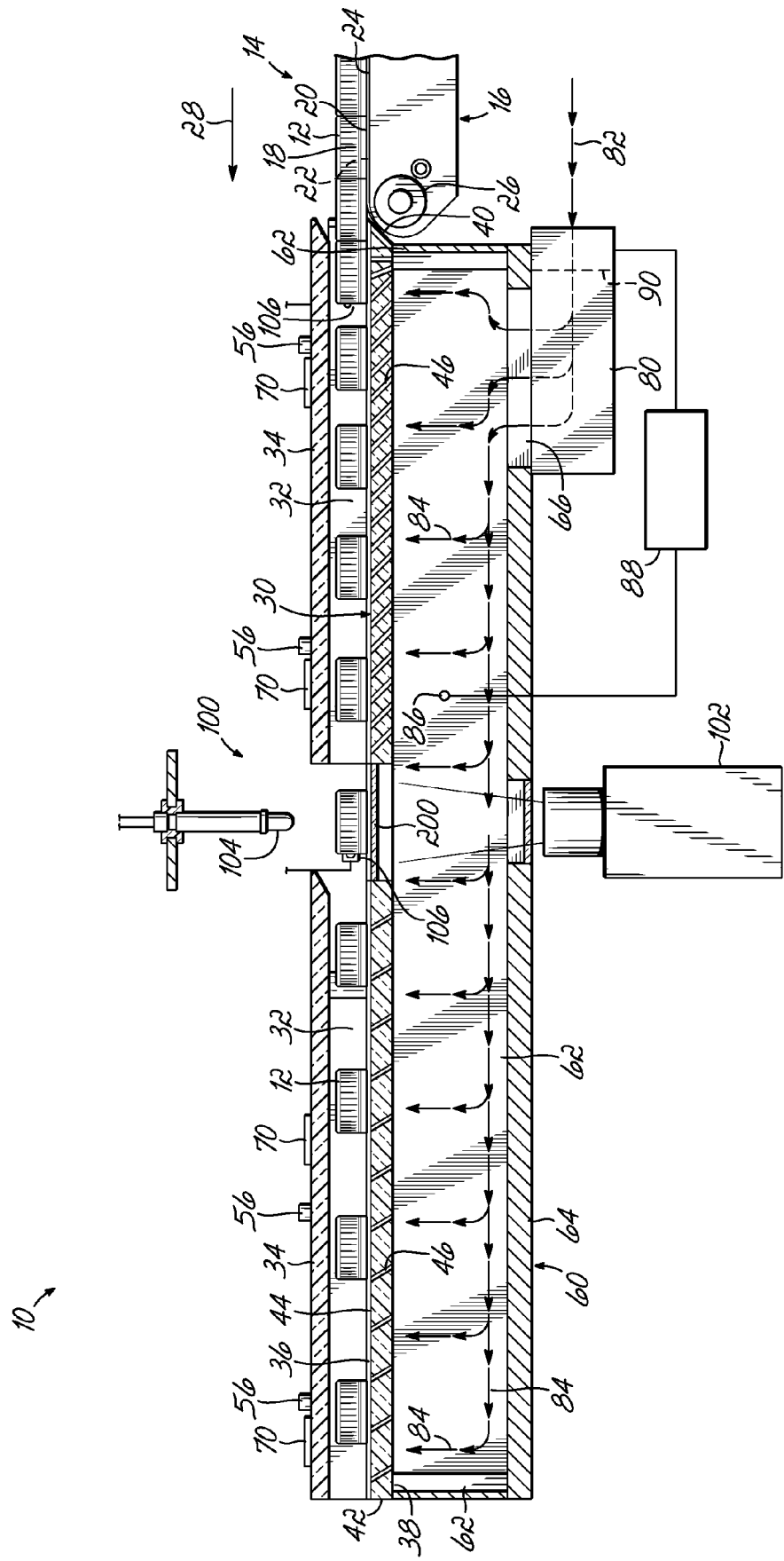
FIG. 10 is a cross-sectional front view of a second embodiment of this invention where the light source and the camera are reversed from the first embodiment.
Figure 11:
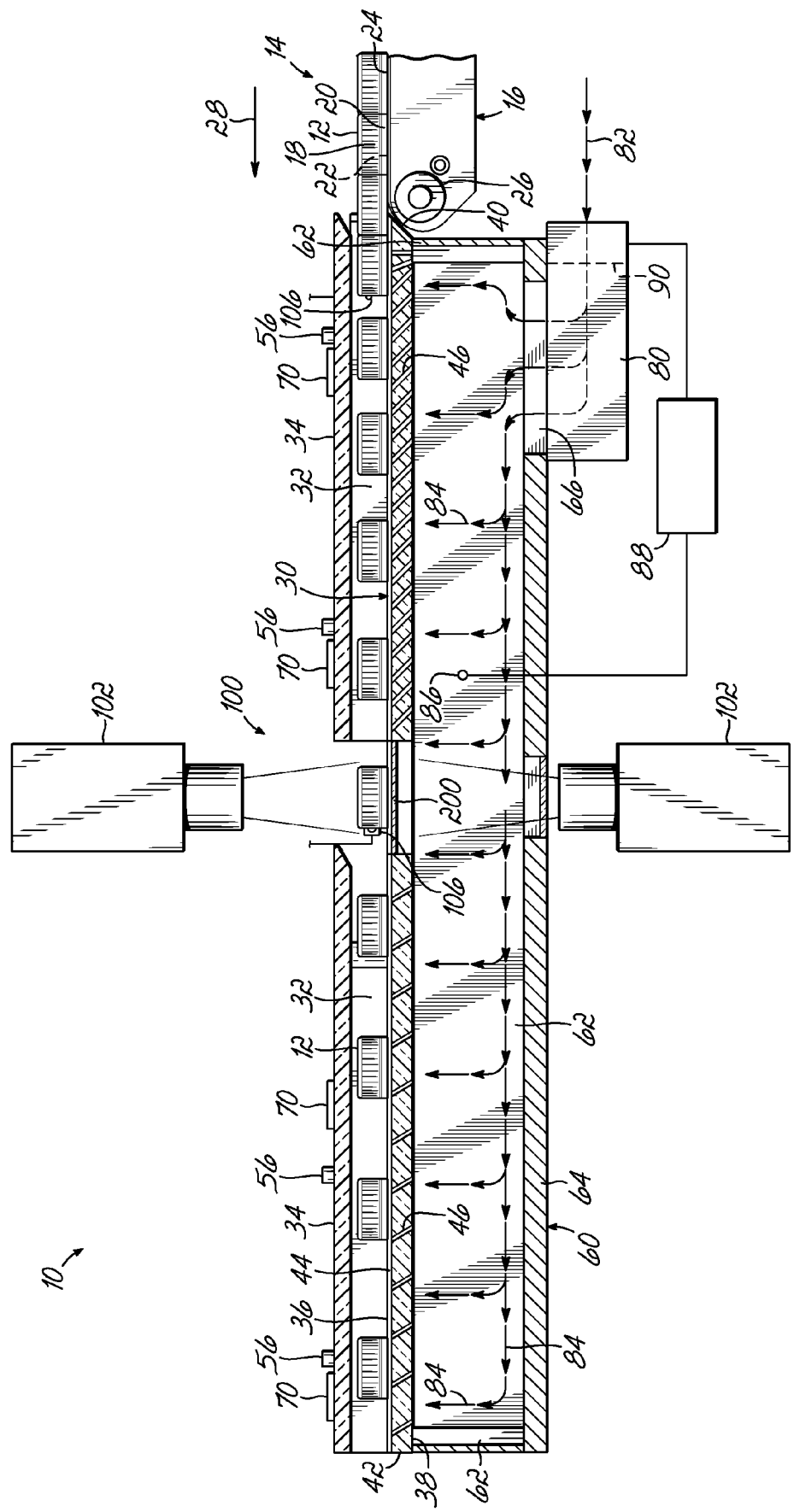
FIG. 11 is a cross-sectional front view of an alternative second embodiment of this invention where two cameras are used to capture images of each work piece.

A second embodiment of this invention is shown in FIGS. 10-11. The second embodiment contains all the elements as the first embodiment described in detail above and in FIGS. 1-9, as well as one additional feature. Instead of the inspection conveyor 30 being made completely out of translucent plastic material, an inspection window 200 is placed in the inspection conveyor 30 instead of plastic material at the inspection station 100. This window 200 can be used where the inspection conveyor 30, guide rails 32, and guide rail cover 34 are each made of a different material than transparent or translucent plastic. The window 200 preferably produces a high diffusion of light and may be created out of glass such as opal glass. The glass segment of the inspection conveyor 30 in this embodiment does not interfere with or change the orientation of air holes 46 extending throughout the inspection conveyor 30.

The second embodiment also enables a user to set up the inspection station elements in different ways. In FIG. 10 the light source 104 and the camera 102 have been reversed so that the camera captures images of the work pieces 12 from the lower side of the inspection conveyor 30. Another alternative setup is shown in FIG. 11, where two cameras 102 are located perpendicular to the stream of work pieces 12 with one below the inspection conveyor 30 and one above the inspection conveyor 30. Therefore the second embodiment allows for a wide variety of work pieces 12 to be inspected by the system 10, including work pieces 12 more solid and less translucent than plastic molded bottle caps. All the advantages of the first embodiment are present in the second embodiment, and the invention overcomes the difficulties of known industrial part visual inspection systems.

One skilled in the art will appreciate that both embodiments can be used by a similar method to analyze and inspect a quantity of work pieces. This method includes feeding work pieces to an inspection conveyor, separating and moving adjacent work pieces by funneling pressurized air to the rear surfaces of the work pieces, inspecting the work pieces by illuminating them with a light source and capturing an image with a camera, analyzing these images against quality control standards, and rejecting defective work pieces from the flow of non-defective work pieces, which are discharged at the end of the inspection conveyor.

This invention is not to be limited by what has been particularly shown and described, except as indicated by the following claims.

What is claimed is:

1. An inspection system for inspecting each of a series of serially fed work pieces in a stream of work pieces, the inspection system comprising:
    an inspection conveyor having a first end, a second end, and a plurality of air holes in communication with the inspection conveyor, wherein each of the work pieces is serially received at the first end and discharged at the second end;
    a passage from the first end of the inspection conveyor to the second end of the inspection conveyor;
    an air blower which provides pressurized air through the air holes in order to accelerate and separate each of the work pieces along the inspection conveyor;
    wherein the air holes located proximate the first end have a different spacing relative to each other than the air holes located proximate the second end;
    an inspection station located intermediate the first end and the second end of the inspection conveyor, the inspection station including a light source and a camera, the light source being positioned to illuminate each of the work pieces at the inspection station for imaging by the camera;
    a processing unit operably coupled to the camera to analyze images of the work pieces generated by the camera with respect to predetermined quality control standards; and
    a rejection mechanism operably coupled to the processing unit to receive a control signal from the processing unit, the rejection mechanism being operable to remove selected work pieces from the inspection conveyor based on the control signal.

2. The inspection system of claim 1, further comprises:
    a feed conveyor to serially feed the work pieces, each of which is in contact with adjacent work pieces on the feed conveyor.

3. The inspection system of claim 1, wherein the inspection conveyor further comprises a shallow groove running lengthwise down the center of the top surface of the inspection conveyor, the shallow groove adapted to allow work pieces with non-planar surfaces to slide along the inspection conveyor without dragging.

4. The inspection system of claim 1, wherein the inspection conveyor is created from translucent plastic material.

5. The inspection system of claim 1, wherein the passage further comprises:
   at least two guide rails coupled to the top surface of the inspection conveyor;
   a guide rail cover coupled to each of the guide rails;
   wherein the guide rails and guide rail cover are adjustable to size the passage for different sizes and shapes of the work pieces.

6. The inspection system of claim 1, further comprising:
   a variable speed drive mechanism operatively coupled to the air blower;
   an air pressure sensor; and
   a controller which receives readings from the air pressure sensor and modifies the speed of the variable speed drive mechanism to maintain a constant air pressure through the air holes of the inspection system.

7. The inspection system of claim 6, wherein the air blower further comprises a filter adapted to keep containments out of the inspection system, the filter being monitored by the controller so that the filter can be replaced when the filter becomes ineffective.

8. The inspection system of claim 1, wherein the inspection conveyor contains one vertical air hole at the inspection station.

9. The inspection system of claim 1, wherein the passage has an opening at the inspection station adapted to allow defective work pieces to be removed from the passage by the rejection mechanism.

10. The inspection system of claim 1, wherein the plurality of air holes in the inspection conveyor are arranged in a single longitudinal line.

11. The inspection system of claim 10, further comprising:
    a trigger operably coupled to the air holes and activated by the passing of a work piece;
    an air valve controlling flow of pressurized air into the air holes; and
    a control mechanism which controls the timing and duration of an air blast coming through the air valve whenever the trigger is activated.

12. The inspection system of claim 1, wherein the inspection conveyor further comprises a window at the inspection station adapted to allow the light source and the camera to be reversed or alternatively, two cameras to be used to inspect both sides of each work piece.

13. The inspection system of claim 1, wherein the inspection station further comprises a trigger positioned to detect a work piece entering the inspection station and to send a control signal to activate the camera and the processing unit.

14. The inspection system of claim 1, wherein the light source is an infrared light source.

15. An inspection system for inspecting each of a series of serially fed plastic molded bottle caps in a stream of bottle caps, the inspection system comprising:
    a feed conveyor to serially feed the bottle caps, each of which is in contact with adjacent bottle caps on the feed conveyor;
    an inspection conveyor disposed generally horizontally and having a first end, a second end, and a plurality of air holes extending from a bottom surface of the inspection conveyor to a top surface of the inspection conveyor, wherein each of the bottle caps is serially received at the first end from the feed conveyor and discharged at the second end;
    at least two guide rails coupled to the top surface of the inspection conveyor;
    a guide rail cover coupled to each of the guide rails so that a passage is provided from the first end of the inspection conveyor to the second end of the inspection conveyor;
    an air blower that provides pressurized air through the air holes in order to accelerate and separate each of the bottle caps along the inspection conveyor;
    wherein the air holes located proximate the first end have a different spacing relative to each other than the air holes located proximate the second end;
    an inspection station located intermediate the first end and the second end of the inspection conveyor, the inspection station including a light source and a camera, the light source being positioned to illuminate each of the bottle caps at the inspection station for imaging by the camera;
    a processing unit operably coupled to the camera to analyze images of the bottle caps generated by the camera with respect to predetermined quality control standards;
    a trigger which detects a bottle cap entering the inspection station and sends a control signal to activate the camera and the processing unit; and
    a rejection mechanism operably coupled to the processing unit to receive a control signal from the processing unit, the rejection mechanism being operable to remove selected bottle caps from the inspection conveyor based on the control signal.

16. The inspection system of claim 15, wherein the feed conveyor delivers about 1600 bottle caps per minute to the inspection conveyor.

* * * * *